United States Patent [19]
Baxter et al.

[11] Patent Number: 5,383,765
[45] Date of Patent: Jan. 24, 1995

[54] AIR FRESHENER APPARATUS FOR CEILING FANS

[75] Inventors: James T. Baxter, Hahira; Doug M. Vick; George S. Gibbs, both of Thomasville, all of Ga.

[73] Assignee: New Ideas International, Thomasville, Ga.

[21] Appl. No.: 971,344

[22] Filed: Nov. 4, 1992

[51] Int. Cl.6 ............................................. F04D 29/00
[52] U.S. Cl. ................................. 416/62; 416/146 R; 261/84; 422/5; 422/124
[58] Field of Search ..................... 416/5, 62, 146 R; 261/84; 422/1, 5, 120, 124; 239/34, 57, 55, 282, 283; D23/366

[56] References Cited

U.S. PATENT DOCUMENTS

| D. 247,249 | 2/1978 | Schimanski | D23/150 |
| D. 308,721 | 6/1990 | Ahl | D23/366 |
| D. 324,910 | 3/1992 | Portis | D23/366 |
| D. 329,282 | 9/1992 | Petersimes et al. | D23/366 |
| 3,804,330 | 4/1974 | Miller et al. | 239/34 |
| 3,844,478 | 10/1974 | Davis | 239/57 |
| 4,219,145 | 8/1980 | Jaeschke et al. | 229/8 |
| 4,662,823 | 5/1987 | Cooke | 416/5 |
| 4,753,573 | 6/1988 | McKnight | 55/316 |
| 4,889,543 | 12/1989 | Burt | 55/97 |
| 4,944,898 | 7/1990 | Glaser | 261/84 |
| 5,022,819 | 6/1991 | Murcin et al. | 416/62 |

OTHER PUBLICATIONS

Fan Scents TM product card, Lines Unlimited, Inc. Chicago, Ill.

Primary Examiner—Edward K. Look
Assistant Examiner—James A. Larson
Attorney, Agent, or Firm—Kennedy & Kennedy

[57] ABSTRACT

An air freshener apparatus having a recess defined by a tray, two sidewalls extending upwardly therefrom with overlapping flanges, and an upstanding end wall slidably received on a blade of a ceiling fan with a foam pad impregnated with a scent material received in the recess. Two hook-like arms extend outwardly from the tray for slidingly holding the air freshener apparatus on an upper surface of the fan blade.

5 Claims, 2 Drawing Sheets

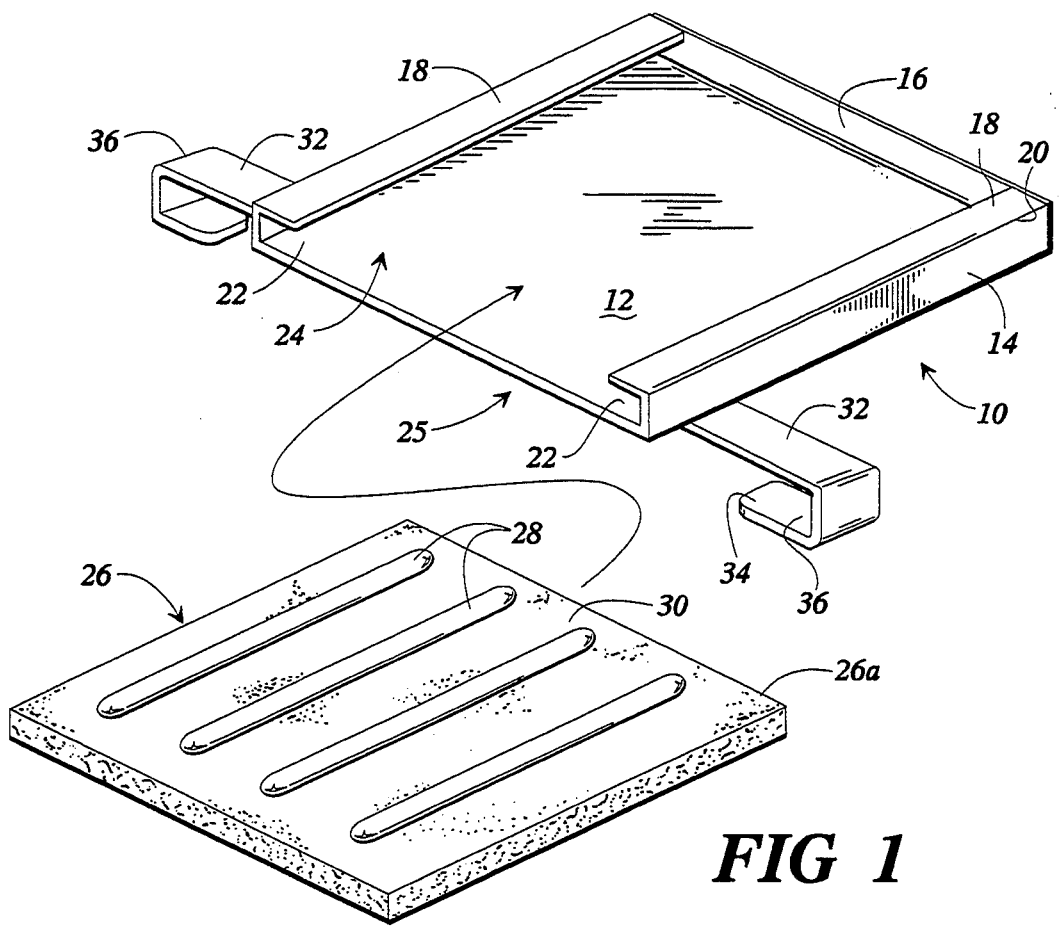
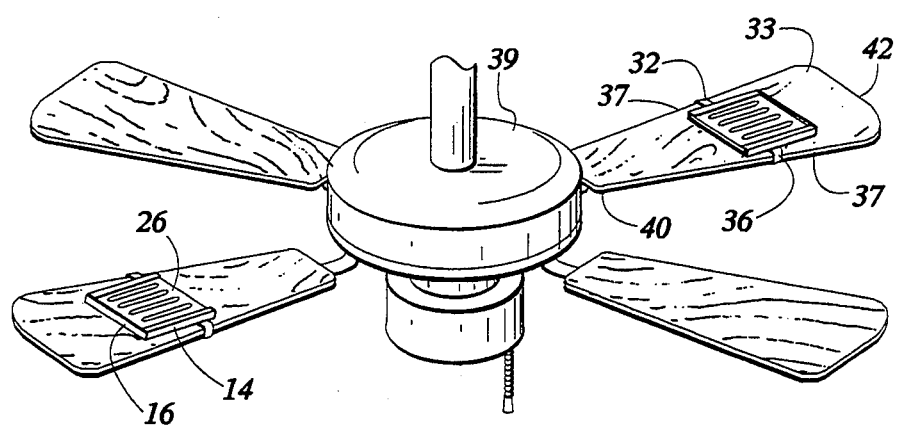

AIR FRESHENER APPARATUS FOR CEILING FANS

TECHNICAL FIELD

The present invention relates to air fresheners. More particularly, the present invention relates to an air freshener having a slidably replaceable scent material that mounts to a fan blade of a ceiling fan.

BACKGROUND OF THE INVENTION

The use of ceiling fans has increased in response to increased costs for cooling and heating of homes, offices, restaurants, and like facilities. Operation of the ceiling fans stirs the air and causes the air to circulate. Warmed air that collects near the ceiling moves to the floor; cool air that collects near the floor moves to the ceiling. Such circulation of air makes more effective use of the heated or cooled air. Movement of the air further distributes odors and smells that may occur in a room. Such odors may arise from cooking of foods, burning wood in fireplaces, smoking cigarettes and pipes, and the like. Often it is desirable to deodorize a room to eliminate such obnoxious odors. In other circumstances, a pleasant odor may provide simply a refreshing atmosphere for a room in which persons gather.

There are devices in the prior art which cooperate with ceiling fans to deodorize the air of a room. For example, U.S. Pat. No. 4,944,898 issued to Glaser describes an air freshener dispenser with a mounting element that is fixed to a fan blade by an adhesive. A case releasably joins with a hook-and-loop fastener to the mounting element. The case contains an air freshening material. Slots in the case expose the air freshening material to the air in the room.

U.S. Pat. No. 5,022,819 issued to Murcin et al describes a deodorizing device which clips to a fan blade to hold a scent package thereon. A pair of U-shaped clip members have legs that terminate in U-shaped end portions. The end portions surmount about the lateral edges of a fan blade. Spring members or straps connect between the clip members and overlie the air freshener package which contains a scent.

While accomplishing the goal of deodorizing the air in a room, these devices still have drawbacks. The devices are securely fixed to the fan blade, such as with adhesive, springs, or straps. Such attachment may require special installation or assembly of parts for removably fixing the device. Improper positioning of a device may create an imbalance for the fan, resulting in wobble and in erratic performance. A device fixed with adhesive may be difficult to remove and reposition. A device removedly fixed with springs requires assembly of interlocking parts which slidingly engage the lateral edges of the fan blade. The scent package must be properly positioned with the springs to assure that the package does not fly off during operation of the fan.

Springs or elastomeric straps, however, may permit the device to slide outwardly during high rotation of the fan. Slippage of a device on one fan blade may cause the fan to become unbalanced during operation. An unbalanced fan risks damage to the fan or nearby articles or possible injury to persons.

The scent material must also be replaced after exhaustion. In some prior art devices, replacement of the scent material involves removal of the old spent case and installation of a new case fitted with scent material. For another device, replacement of the scent material may require partial disassembly of the device.

Therefore there is a need in the art for an air freshener that mounts easily to a fan blade and that facilitates replacement of the scent material.

SUMMARY OF THE PRESENT INVENTION

Generally described, the present invention provides an air freshener apparatus that slidably mounts to a tapered fan blade for receiving means for emitting a deodorizing scent.

More particularly described, the air freshener apparatus comprises a tray with two upstanding sidewalls and an end wall. The sidewalls are L-shaped to have an upper flange extending towards the opposite sidewall. The sidewalls and the end wall define a recess for receiving a foam pad impregnated with a scent material. Hook-like arms extend outwardly from the tray and slidably engage the lateral sides of the fan blade so that the apparatus does not fly off of the blade during operation of the fan. The end wall and the sidewalls hold the foam pad in the tray.

Accordingly, it is an object of the present invention to provide an air freshener apparatus for ceiling fans.

It is another object of the present invention to provide an air freshener apparatus that easily installs on a ceiling fan.

It is another object of the present invention to provide an air freshener apparatus that easily receives a scent material for deodorizing air.

It is another object of the present invention to provide an air freshener apparatus that mounts to a blade of a ceiling fan for deodorizing air during operation of the fan.

It is another object of the present invention to provide a self-balancing air freshener apparatus for a ceiling fan.

These and other objectives, features, and advantages will become apparent from a reading of the following detailed description of the invention and claims in view of the appended drawings.

BRIEF DESCRIPTION OF THE DRAWINGS

FIG. 1 is an upper and left perspective view of an air freshener apparatus constructed in accordance with the present invention, with a pad impregnated with scent material exploded therefrom.

FIG. 2 is an upper and left perspective view of a ceiling fan with the air freshener apparatus illustrated in FIG. 1 attached to a blade of the fan.

DETAILED DESCRIPTION

Figure 3:
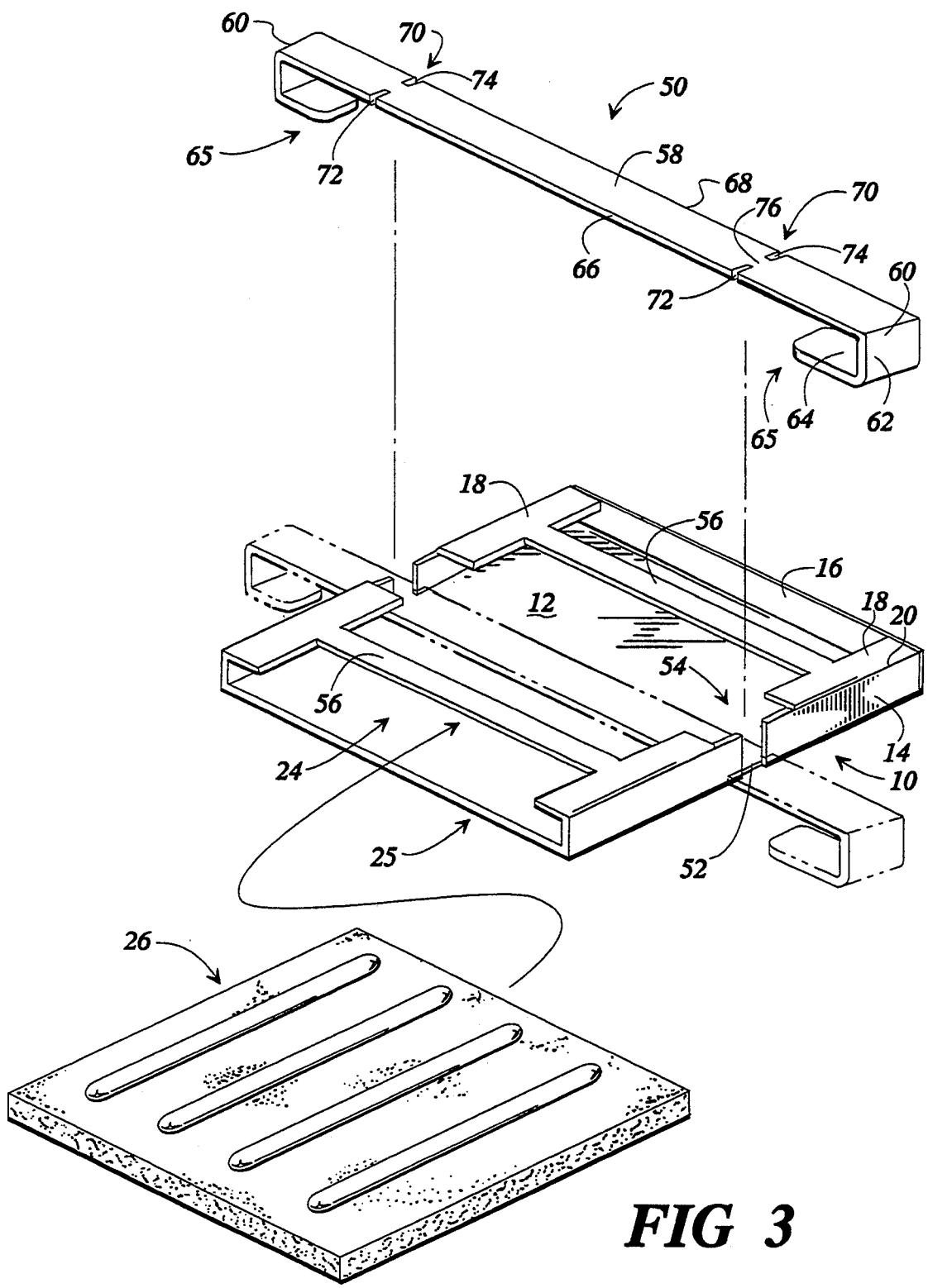
FIG. 3 is an exploded upper and left perspective view of a preferred air freshener apparatus with an insertable cross arm, constructed in accordance with the present invention.

Referring now in more detail to the drawings, in which like numerals indicate like parts throughout the several views, FIG. 1 shows an upper and left perspective view of an air freshener apparatus 10 constructed in accordance with the present invention. The air freshener apparatus 10 comprises a planar tray 12 having a pair of upstanding sidewalls 14 and an upstanding end wall 16. The sidewalls 14 in cross-sectional view are L-shaped. Each sidewall 14 has a flange 18 along an upper portion of the sidewall, for a purpose discussed below. Each of the flanges 18 extend inwardly towards the opposite sidewall 14 and covers a portion 22 of the tray 12. In the illustrated embodiment, the flanges 18 extend inwardly from an upper edge 20 of the respective sidewall 14. An alternate embodiment (not illustrated) includes a third flange that extends inwardly from the upper edge of the end wall 16.

The sidewalls 14 and the end wall 16 cooperate with the tray 12 to define a recess 24 with an open end 25 in the tray. The recess 24 receives a scent material for emission as a deodorant. In the illustrated embodiment, the recess 24 receives a foam pad 26 which includes a scent material 28. The scent material 28 is applied to an upper surface 30 of the foam pad 26. The foam pad 26 is sized for being slidingly received within the recess 24 through the open end 25. The scent preferably is embedded in the scent material 28 which is applied to the foam pad 30. The scent material 28 is exposed to moving air as the fan operates, and the emitted scent deodorizes the air.

The flanges discussed above hold the foam pad 26 in the tray 22. The flanges restrict the foam pad 26 from exiting the tray 12 during operation of the ceiling fan to which the apparatus 10 is attached. Another alternate embodiment (not illustrated) includes a grid or lattice connected between the sidewalls 14 for this purpose.

In a preferred embodiment, the scent material 28 is a hot melt glue applied in a heated viscous state to the foam pad 26. The fluidal scent material 28 partially migrates into the foam pad 26. The scent material 28 then cools and cures with a portion of the scent material dried within the interstices of the foam pad 26. This portion anchors the bulk of the scent material 28 to the upper surface of the foam pad 26. In a preferred embodiment, the foam pad 26 is three inches by three inches with four parallel beads of scent material 28.

A pair of arms 32 extend laterally from the tray 12 to hold the apparatus 10 to a fan blade 33, as illustrated in FIG. 2. A distal end 34 of each arm 32 forms an inwardly facing hook 36. Each of the hooks 36 slidingly overlaps a respective lateral edge 37 of the tapered fan blade 23 for holding the air freshener apparatus 10 on the fan blade of a ceiling fan 39. The arms 32 preferably are narrow straps that extend outwardly from the tray 12. It is preferred that the arms 32 be positioned between the open end 25 and the middle of the tray 12. The arms 32 in the illustrated embodiment are integral with the tray 12. The apparatus 10 is preferably molded of a plastic material which is strong, lightweight, and inexpensive. In an alternate embodiment, the arms 32 are narrow thin metal straps which are riveted to the tray 12. The distal end 34 of each metal arm 32 is bent to form the hook 36.

The distance between the hook ends 36 of the arms 32 is intermediate the widths of the tapered fan blade 33 at its narrow end 40 and its wide end 42 as illustrated in FIG. 2. Known fan blades typically taper about 1 to 2 inches from narrow near the fan motor to wide outwardly of the motor. For example, some of these fan blades taper the narrow end to the wide end from 4 inches to 5½ inches; others taper from 5½ inches to 6½ inches. The distance between the hook ends 36 of the arms 32 is preferably about 4 to 5 inches. Most fan blades could be readily accommodated by one of two embodiments. In one embodiment, the distance between the hook ends 36 is 4 11/16 inches; in the other embodiment the distance is 5 11/16 inches.

As illustrated in perspective view in FIG. 2, the air freshener apparatus 10 attaches to the tapered fan blade 33 of the ceiling fan 39 for deodorizing the air of a room. The tray 12 is placed on the upper surface of the fan blade 33 between the ends 40 and 42. The hook ends 36 of the arms 32 extend outwardly from the lateral sides 37 of the fan blade 33. As discussed above, the width between the hooks 36 is intermediate the widths of the narrow and wide ends 40 and 42 of the fan blade 33. The tray 12 is then moved outwardly along the fan blade 33 so that the hooks 36 contact the side edges 37 of the fan blade.

The foam pad 26 is slidingly inserted into the recess 24 through the open end 25 of the tray 12 to abut a leading side 26a of the foam pad against the end wall 16. The flanges 18 overlap the upper surface of the pad 26 to hold the pad in the recess 24.

The ceiling fan 39 is then operated in order to move the scent material 28 through the air for deodorizing. The centrifugal force of the fan 39 pulls the tray 12 outwardly towards the wide end 42 of the blade 33. The tapered blade 33 stops the apparatus 10 from sliding off the spinning blade 33. The hooks 36 reach a maximum extent on the blade 33 where the blade width equals the distance between the hooks. The end wall 16 of the apparatus 10 cooperates with the flanges 18 to hold the foam pad 26 in the recess 24 during operation of the ceiling fan 39. The end wall 16 and the flanges 18 restrict the foam pad 26 from coming out of the recess 24, due to the centrifugal force of the fan.

The air freshener apparatus of the present invention accordingly is self-balancing when used on a fan. A four-blade fan requires at least one pair of the apparatus 10. Each one of the pair is slidingly received on opposite blades. A five-blade fan requires an apparatus 10 on each blade. As the fan rotates, the apparatus 10 on each blade slides an equal distance outwardly on the blade, until the hook ends 36 lock against the side 37 of the blade 33.

An alternate embodiment (not illustrated) is adapted to have laterally adjustable hook ends 36. The hook ends 36 are thereby movable towards and away from the tray so that the apparatus is selectively positionable at a predetermined distance from the fan on the fan blade. Setting the hook ends 36 a greater distance apart results in the apparatus 10 being positioned outwardly on the fan blade 33 a greater distance from the fan 39. In using such adjustable embodiment, care would have to be exercised to set each of the apparatus 10 with the same spacing for the hook ends, in order to keep the fan in balance.

FIG. 3 illustrates an upper and left perspective view of a preferred embodiment of the air freshener apparatus 10 with an insertable cross arm 50 for holding the air freshener apparatus on the fan blade. Each of the side walls 14 includes a notch 52 of a first width and each of the flanges 18 includes a notch 54 of a second width. The notches 52 and 54 are preferably co-axial and aligned with the matching notches in the opposite flange 18. A pair of spaced-apart cross members 56 extend between the side flanges 18, for a purpose discussed below. In the illustrated embodiment, one cross member 56 is disposed on each side of a line defined by the notches 52 and 54 on opposite sides at the tray 12.

The cross arm 50 comprises an elongate member 58 of a predetermined length. The distal ends 60 each include a flange 62 that extends down and a flange 64 that extends inwardly therefrom. The flanges 62 and 64 cooperate to define an L-shape hook 65 at the distal ends 60. In a preferred embodiment, a first side 66 of the elongate member 58 is shorter than a second side 68.

This enables the distal ends 60 to have a slight taper for being matingly received on a tapered blade of a ceiling fan. The taper facilitates the air freshener apparatus 10 slidingly moving outwardly on the fan blade 33. As discussed above, the air freshener apparatus 10 self-balances the ceiling fan during operation thereof. For example, a four-blade fan requires an even number of the air fresheners 10. If two of the air fresheners are used, one is placed on each of an aligned pair of the fan blades. A five-blade fan would use one air freshener 10 on each blade.

The elongate member 58 further includes two sets 70 of a pair of slots 72 and 74 extending inwardly from the sides 66 and 68 respectively. The slots 72 and 74 are aligned and define a gap 76 which is received in the notch 52. The gap 76 accordingly is less than the width of the notch 52. The edges of the notches 52 and 54 extend through the slots 72 and 74, so that the cross arm 50 seats against the planar tray 12 of the air freshener apparatus 10. The distal ends 60 of the cross arm 50 extend outwardly from the side walls 14 with the hook ends 65 disposed downwardly of the tray 12.

The air freshener apparatus 10 illustrated in FIG. 3 is used by first connecting the cross arm 50 to the side walls 14. As discussed above, blades for ceiling fans differ in width. The cross arm 50 having a length appropriate for the fan is selected. For example, cross arms 50 having lengths of 4 11/16 inches or 5 11/16 inches will accommodate most known fan blades. The slots 72 and 74 are aligned with the notches 52 and 54 in the side walls 14. The cross arm 50 is then snapped into place by pressing downwardly thereon towards the inner surface of the tray 12. The slots 72 and 74 have a width slightly greater than the thickness of the side wall 14 for receiving the edge of the notches 52 and 54 therethrough. The longer side 68 if the cross arm 50 is positioned on the side of the tray 12 having the end flange 16. This positions the tapered hooks 65 appropriately for being slidingly received on the tapered blade 33. In an alternate embodiment, arrows or other directional symbols molded into the cross arm 50 and the tray 12 assist positioning the cross arm. In another alternate embodiment, the first notch 52 on one side 18 has a width different than the notch 52 on the opposite side wall. The gap 76 for the respective sets 70 of slots 72 and 74 likewise are of different values, which correspond to the widths of the notches 52. In this manner, the cross arm 50 is inserted so as to facilitate the tray 12 being slidingly received on the fan blade 33.

The foam pad 26 is then slidingly inserted into the recess 24 through the open end 25 of the tray 12. The foam pad 26 slides under the pair of cross members 56 and over the upper surface of the cross arm 50. The cross members 56 hold the foam pad 26 in the recess 24 and restrain the foam pad 26 from coming out of the air freshener 10 during use.

The air freshening apparatus 10 is then attached to one of the fan blades 33 of a ceiling fan. As discussed above, tray 12 is placed on the fan blade 33 with the hook ends 65 outwardly of the lateral sides 37 of the blade. In the illustrated embodiment, the longer side 68 of the cross arm 50 is positioned outwardly of the shorter side 66. The tapered hook ends 65 slidingly pass along the edge 37 until the width of the fan blade 33 exceeds the length of the longer side 68. Other air freshener apparatus 10 are positioned on the fan blades and moved outwardly.

With the appropriate air fresheners 10 positioned on the blades 33, the ceiling fan 39 remains in balance during operation. Centrifugal force pulls each tray 12 outwardly on the respective blade 33 an equal amount, so that the air fresheners 10 balance the fan. The tapered hooks 65 facilitate the air fresheners 10 sliding outwardly on the blade. During operation of the ceiling fan 39, the cross members 56 cooperate with the flanges 18 and end wall 16 to hold the foam pad 26 in the recess 24.

The air freshener apparatus of the present invention provides a self-balancing scented deodorizer for ceiling fans. The operation of the fan positions each apparatus 10 on its respective blade equi-distant from the fan. This maintains the fan in balance during operation. The apparatus rests on the upper surface of the fan blade and is lightweight and unobtrusive.

The specification has thus described various embodiments, including a preferred embodiment, of the present invention, including the assembly and use thereof. It is to be understood, however, that numerous changes and variations may be made in the construction of the present invention. It should therefore be further understood that modification of the present invention may be made without departing from the scope thereof as set forth in the appended claims.

What is claimed is:

1. An air freshener apparatus for a ceiling fan having fan blades that each taper in width from a narrow inner end to a wider outer end, comprising:
   a tray with a pair of upstanding sidewalls and an end wall, each sidewall having a flange extending laterally therefrom along an upper edge toward the opposite sidewall, thereby defining a recess on each side, each sidewall and flange further defining a notch;
   a foam pad impregnated with a scent material, slidingly received in the tray with side edges of the foam pad within the recesses;
   a cross arm received in the notches and having one of a pair of hooks at each distal end, the pair of hooks extending laterally from each respective lateral side of the tray for overlapping a lateral edge of the fan blade,
   whereby the air freshener apparatus, being slidingly received on an outer portion of the tapered fan blade, deodorizes the air.

2. The air freshener apparatus as recited in claim 1, wherein the cross arm defines two sets of a pair of slots for being receiving on an edge of the notches, for attaching the cross arm to the tray.

3. The air freshener apparatus as recited in claim 1, wherein the scent material comprises:
   a hot melt glue applied as a heated viscous fluid on an upper surface of the foam pad; and
   a scent included in the hot melt glue.

4. The air freshener as recited in claim 1 further comprising at least one cross member between the opposing flanges for retaining the foam pad.

5. A method of deodorizing a room, comprising:
   slidingly engaging a tray with each of at least two tapered fan blades of a ceiling fan, each tray having a pair of recesses defined by flanges that extend inwardly from two opposing sidewalls that each include a notch, a cross arm received in the notches with each distal end terminating in a hook which extends outwardly of the sidewalls for engaging a respective side edge of the respective fan blade;
   inserting a foam pad impregnated with scent material into each of the trays with lateral edges of the foam pad received in the recesses of the respective tray; and
   operating the ceiling fan to expose the scent material to the air,
   whereby the trays, being moved outwardly, balance the fan during operation.

* * * * *